United States Patent [19]

Burr et al.

[11] Patent Number: 4,704,899

[45] Date of Patent: Nov. 10, 1987

[54] MEASUREMENT OF PHYSICAL PROPERTIES OF THE SOLID COMPONENT OF A SLURRY

[75] Inventors: Kenneth J. Burr; Laurence S. Smith; David Hazelden, all of St. Austell, United Kingdom

[73] Assignee: English Clays Lovering Pochin & Company, Limited, United Kingdom

[21] Appl. No.: 692,061

[22] Filed: Jan. 16, 1985

[30] Foreign Application Priority Data

Jan. 17, 1984 [GB] United Kingdom ............... 8401192

[51] Int. Cl.$^4$ .......................................... G01N 15/00
[52] U.S. Cl. ................................... 73/61 R; 73/61.4; 73/863.23
[58] Field of Search ................. 73/61.4, 61 R, 63, 53, 73/863.23, 863.25, 864.31, 864.34; 422/62; 162/DIG. 10, DIG. 11; 210/96.1

[56] References Cited

U.S. PATENT DOCUMENTS

| 2,276,841 | 3/1942 | Hanson | 73/61 R |
| 2,672,431 | 3/1954 | Goetz | 73/61 R |
| 2,677,467 | 5/1954 | Giorgini | 210/198 |
| 3,289,467 | 12/1966 | Parker et al. | 73/61.4 |
| 3,575,691 | 4/1971 | Pollard | 23/253 |
| 3,746,167 | 7/1973 | Arthur | 210/70 |
| 3,893,333 | 7/1975 | Sunahara et al. | 73/61 R |
| 4,066,359 | 1/1978 | Bucalo | 73/61 R |
| 4,357,667 | 11/1982 | Skorlos | 73/61 R |

FOREIGN PATENT DOCUMENTS 1910641 9/1970 Fed. Rep. of Germany .
WO83/04309 12/1983 PCT Int'l Appl. .
894459 4/1962 United Kingdom .
1040080 8/1966 United Kingdom .
1201833 8/1970 United Kingdom .
1228284 4/1971 United Kingdom .
1247274 9/1971 United Kingdom .
1354286 5/1974 United Kingdom .
1444759 8/1976 United Kingdom .
1489067 10/1977 United Kingdom .
1490362 11/1977 United Kingdom .
2055466 4/1981 United Kingdom .
2077132 12/1981 United Kingdom .
2133306 7/1984 United Kingdom .

Primary Examiner—Michael J. Tokar
Assistant Examiner—Hezron E. Williams
Attorney, Agent, or Firm—Stefan J. Klauber

[57] ABSTRACT

A physical property of the solid component of a slurry, for example the percentage content of a selected element such as iron, is continuously measured. A sampling device (2) carrying a filter element is immersed in the slurry at a sampling station (A). Vacuum is applied to the sampling device (2) to cause the liquid content of the slurry to pass through the filter element, leaving the solid component deposited on the filter element as a filter cake. The sampling element is transferred to a heating station (B), where the filter cake is dried, and then to a measuring station (C), where the desired physical property is measured. The sampling device is then transferred to a washing station (D), where the filter cake is washed from the filter element so that the procedure can start again. The process is automatically controlled by a microprocessor, enabling continuous sampling of the slurry to be carried out.

15 Claims, 2 Drawing Figures

MEASUREMENT OF PHYSICAL PROPERTIES OF THE SOLID COMPONENT OF A SLURRY

FIELD OF THE INVENTION

This invention relates to the measurement of a physical property of the solid component of a slurry.

BACKGROUND OF THE INVENTION

It is useful, particularly in the clay industry, to have information on the physical properties of the solid phase in clay slurry. In particular, it is useful to know the percentage content of elements such as iron and potassium. The usual method of obtaining this information is for a sample of the slurry to be collected and taken to a laboratory where it is dried and analysed in the form of a dry powder. This is a time-consuming process, and does not permit continuous monitoring of the slurry.

SUMMARY OF THE INVENTION

According to one aspect of the present invention, there is provided a device for use in the preparation of a test sample of the solid component of a slurry, the device comprising a chamber bounded at least partly by a porous wall for supporting a filter element on the face of the wall away from the chamber, the device having connector means for connection to a vacuum source to place the chamber in communication with the vacuum source, and connecting means for connecting the device to transport means for displacing the device from one operative station to another.

According to another aspect of the present invention there is provided apparatus for measuring a physical property of the solid component of a slurry, the apparatus comprising:
a container for the slurry;
a measuring station provided with a measuring unit;
a device for use in the preparation of a test sample of the solid component, the device comprising a chamber bounded at least partly by a porous wall for supporting a filter element on the face of the wall away from the chamber;
transport means for displacing the device from a sampling position, in which the porous wall is immersed in a slurry in the container, and a measuring position at the measuring station; and
a vacuum source and means for placing the vacuum source in communication with the chamber of the device to cause, in operation, when the device is in the sampling position, the liquid component of the slurry to pass through a filter element on the porous wall of the device leaving the solid component deposited on the filter element as a filter cake.

According to a third aspect of the present invention there is provided a method of measuring a physical property of the solid component of a slurry, the method comprising:
causing the liquid component of the slurry to pass through a filter element immersed in the slurry, leaving the solid component deposited on the filter element as a filter cake; and
displacing the filter element with the filter cake to a measuring station; and
measuring the physical property of the solid component at the measuring station.

In some circumstances, the filter cake deposited on the filter element may be sufficiently dry for the purposes of analysis, but preferably the method includes a drying step, and consequently the preferred apparatus includes a drying station at which the device can be positioned after it has left the container. A heater may be provided at the drying station for driving off remains of the liquid component in the filter cake.

To enable the method to be continuous, the filter element may be washed after each measuring step in order to remove the previously investigated dry sample. After washing, the device may be returned to the container to collect a fresh sample. In the preferred apparatus, the washing step is performed at a washing station at which jets of washing liquid, such as water, are directed at the filter element. Further washing liquid may be fed to the chamber in the device to pass through the filter element to provide a backwashing effect. Apparatus in accordance with the present invention preferably includes control means, such as a microprocessor, for automatically controlling the operation of the apparatus.

DETAILED DESCRIPTION OF A PREFERRED EMBODIMENT

Figure 1:
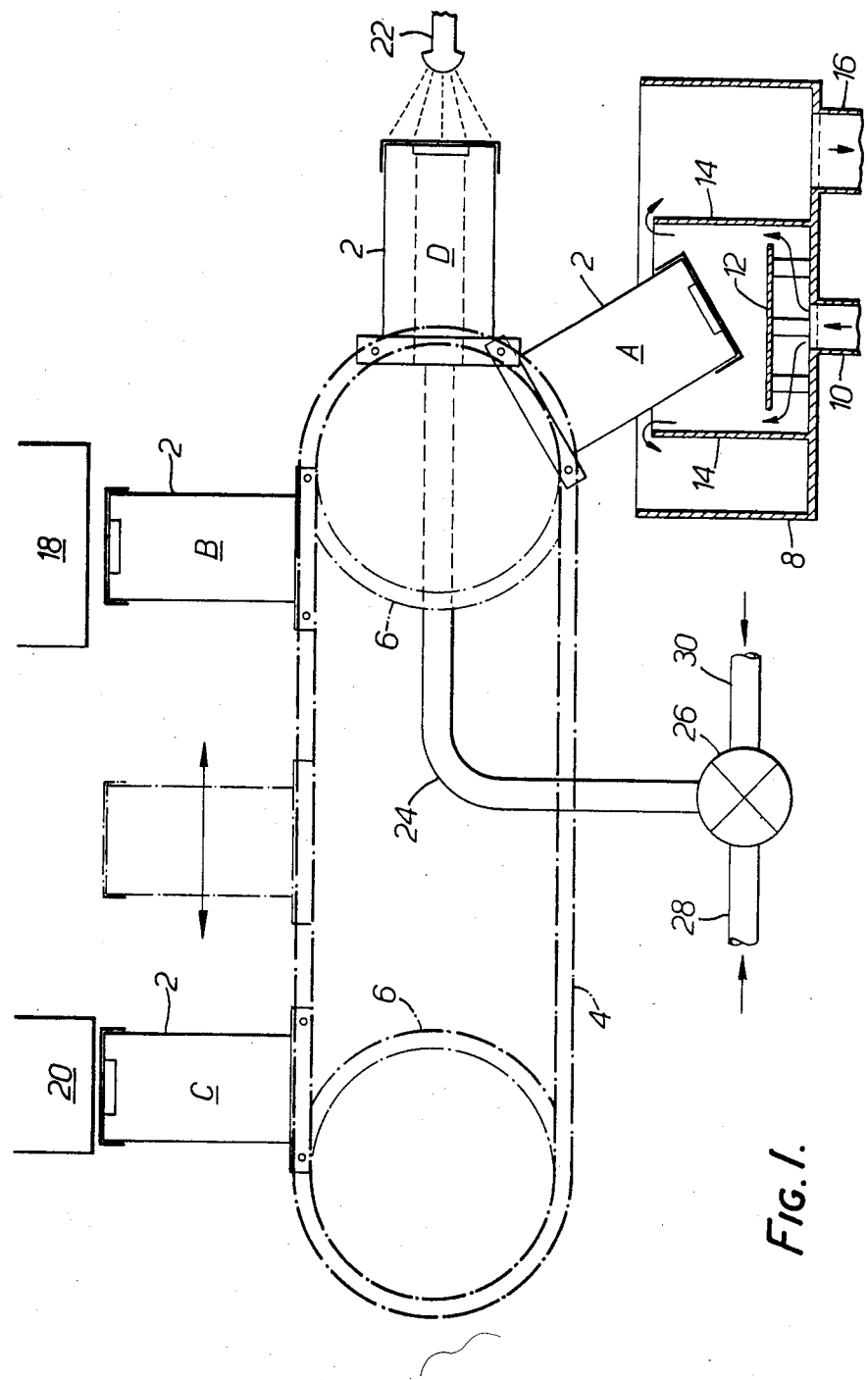
FIG. 1 shows diagrammatically apparatus for measuring the iron content of clay slurry.

The apparatus of FIG. 1 comprises a sampling device 2 which is shown, in full outline, at four stations A, B, C and D. The device 2 is shown in phantom at a position between the stations B and C. Although the apparatus comprises only one sampling device 2, sampling devices are shown at each station A, B, C, D for the sake of clarity.

The sampling device 2 is movable between the stations by transport means in the form of a chain conveyor 4, which runs over chain wheels 6. The conveyor 4 is driven by a stepping motor to position the sampling head 2 accurately at each station.

Station A comprises a sampling station. At station A, there is a constant head container 8 having an inlet 10. A baffle 12 is provided above the inlet 10 in order to provide a smooth flow of slurry into the container. The container 8 is provided with internal partitions 14 over which the slurry flows before passing to an outlet 16.

Station B is a drying station at which a heater 18 is provided. Station C is a measuring station at which a measuring unit 20 is provided. The measuring unit 20 may, for example, be an X-ray fluorescence (XRF) analyser for determining the percentage content, by weight, of the element under investigation (i.e. iron). Alternatively, the analyser may be adapted to measure potassium content, or the content of any one of a number of other elements. The measuring station may, for example, be provided with two or more measuring units 20 for measuring the contents of different elements. A suitable analyser is the "LAB-X 100" analyser available from Oxford Analytical Instruments Limited of Oxford, England.

Station D is a washing station, and is provided with a spraying device 22 for directing jets of water at the sampling device 2.

A flexible pipe 24 extends between the sampling device and a valve 26. The valve 26 is connected to a vacuum pipe 28 and a water supply duct 30.

Figure 2:
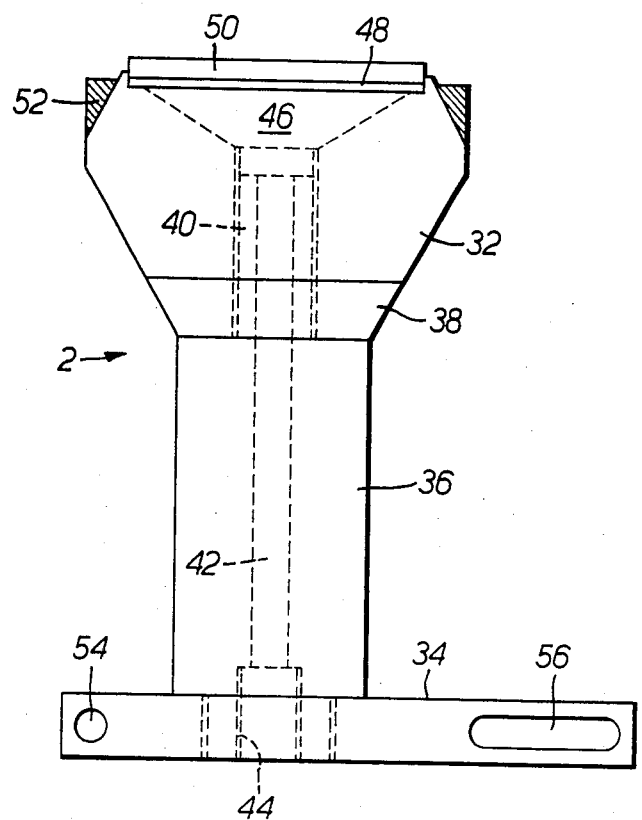
FIG. 2 shows a sampling device of the apparatus of FIG. 1.

FIG. 2 shows the sampling device 2 in more detail. The device 2 comprises a head 32 which is mounted on a stem 36 provided with a base plate 34. The base plate 34 is provided with an aperture 54 and a slot 56 for use in connecting the sampling device to the chain 4. The stem 36 has a threaded spigot 40 which cooperates with a tapped bore in the head 32 to secure the head 32 to the stem 36. A washer 38 made, for example, of TUFNOL (Registered Trade Mark), is provided between the head 32 and the stem 36 to minimise the conduction of heat from the head 32 to the stem 36. The base plate 34 and the stem 36 (including the spigot 40) are provided with a duct 42 which, at its end away from the head 32, is provided with a tapped counter bore 44 for receiving an end fitting of the flexible pipe 24.

The duct 42 emerges into a chamber 46 in the head 32, this chamber 46 being bounded by a perforated back plate 48 on which lies a flat sintered glass filter plate 50. A retaining ring 52 is provided on the head 32 for holding in place a filter element, in the form of a filter cloth (not shown) lying over the filter plate 50.

The operation of the apparatus is controlled automatically by a microprocessor, for example an Intel iSBC 80/10B Single Board Computer. The operation of the apparatus will be described taking station A as the starting point.

When the sampling device moves to station A, the filter cloth of the head 2 is dipped into the slurry in the constant head part of the container 8. The valve 26 is operated to connect the flexible duct 24 to the vacuum source through the vacuum pipe 28. Thus the duct 42 and the chamber 46 are subjected to vacuum, and this causes the liquid component (i.e. water) of the slurry to be drawn through the filter cloth, the filter plate 50 and the back plate 48, leaving the solid component of the slurry deposited on the filter cloth. The device 2 remains in the slurry for a predetermined time selected in dependence on the solids content of the slurry, in order to obtain a filter cake of the required thickness. When this predetermined time has elapsed, the chain 4 is displaced by a stepping motor (not shown) to move the sampling device 2 out of the slurry in the container 8. It will be appreciated that the flexibility of the pipe 24 permits the displacement of the sampling device 2. The sampling device 2 is moved to station B, with vacuum still applied, where it is brought to rest with the filter cake exposed to the heater 18. The sampling device 2 remains at station B for a predetermined drying time sufficient to drive off substantially all of the liquid component remaining in the filter cake. When this time has elapsed, the chain 4 is moved again to transfer the sampling device 2 to the measuring station C. Where the measuring unit 20 is an XRF unit, the radiation source and detectors of the unit are moved into a measuring position, under the control of the microprocessor, on a movable parallelogram assembly. When the measurements have been made, the microprocessor calculates the percentage content of the element under consideration. The percentage figure is printed to two decimal places, the print out also showing the time and date. The result is also displayed on a remote indicator and stored in a battery backed RAM. Where more than one measuring unit is provided at the measuring station, the sampling device 2 is advanced to the next unit where the measuring process is repeated to determine the content of another element.

When the measurement is complete, the sampling device 2 is moved back towards station A, but is stopped at station D where the filter cake is washed off by jets of water issued from the spraying device 22 and by means of backwashing water from the water supply duct 30 passing through the valve 26, the flexible pipe 24 and the duct 42. When washing is complete, the sampling device 2 is returned to the container 8 to collect the next sample.

It will be appreciated that slurry flows continuously through the container 8 from the inlet 10 to the outlet 16, so that the apparatus provides continuous sampling of the flow, enabling changes in the composition of the slurry to be recorded promptly as they occur. The microprocessor may include additional facilities, in order, for example, to obtain an average figure, over a preselected time, for the element under consideration, or to provide a bulk sample figure. The apparatus may also have facilities for manually controlling the various operations of the apparatus.

Because sampling may be continuous, the apparatus and method of the present invention may be used in the automatic control of a process.

Thus, a process for producing a slurry from a plurality of streams of slurrry, the solid components of which have a physical property which differs in the two slurries, may comprise:

(a) blending the streams of slurry to produce a slurry product;

(b) causing the liquid component of the slurry product to pass through a filter element immersed in the slurry product, leaving the solid component deposited on the filter element as a filter cake;

(c) displacing the filter element with the filter cake to a measuring station;

(d) measuring the physical property of the said component at the measuring station;

(e) comparing the measured value for the physical property with a desired value; and (f) adjusting the proportions in which the streams of slurry are blended in order to achieve a slurry product in which the physical property is closer to the desired value.

For example, the apparatus may be used to monitor the potassium content of a blend of kaolin clay streams having respectively high and low potassium contents and to control the proportion in which the streams are blended in order to give a desired product.

We claim:

1. A device for use in the preparation of a test sample of the solid component of a slurry, the device comprising:

an elongate stem;
a head mounted on the elongate stem;
a chamber provided in the head;
a porous wall, at least partly bounding the chamber, for supporting a filter element on the face of the wall away from the chamber;
connector means for connection to a vacuum source to place the chamber in communication with the vacuum source;
connector means provided on the elongate stem for connecting the device to transport means for displacing the device from one operative station to another; and
a duct provided in the elongate stem for providing communication between the connector means and the chamber.

2. A device as claimed in claim 1, in which retaining means is provided for retaining a filter element on the face of the porous wall.

3. A device as claimed in claim 1, in which the porous wall comprises a sintered glass filter plate and a perforated back plate on which the filter plate is supported.

4. Apparatus for measuring a physical property of the solid component of a slurry, the apparatus comprising:
 a container for the slurry;
 a measuring station provided with a measuring unit;
 a device for use in the preparation of a test sample of the solid component, the device comprising a chamber and a porous wall at least partly bounding the chamber, for supporting a filter element on the face of the wall away from the chamber;
 transport means for displacing the device from a sampling position, in which the porous wall is immersed in a slurry in the container, and a measuring position at the measuring station; and
 a vacuum source and connector means for placing the vacuum source in communication with the chamber of the device to cause, in operation, when the device is in the sampling position, the liquid component of the slurry to pass through a filter element on the porous wall of the device leaving the solid component deposited on the filter element as a filter cake.

5. Apparatus as claimed in claim 4, in which drying means is provided for drying the filter cake.

6. Apparatus as claimed in claim 4, in which washing means is provided for washing the filter cake from the filter element.

7. Apparatus as claimed in claim 6, in which the washing means comprises spraying means for directing jets of washing, liquid at the filter element.

8. Apparatus as claimed in claim 4, in which means is provided for supplying washing liquid to the chamber in the device to provide back washing through the filter element.

9. Apparatus as claimed in claim 4, in which the container comprises a constant head container and, in operation, a continuous flow of slurry passes through the container.

10. A method of measuring a physical property of the solid component of a slurry, the method comprising:
 immersing a sampling device in the slurry, the sampling device being mounted on transport means and comprising a porous wall partially defining a chamber, the porous wall supporting a filtering element;
 placing the chamber in communication with a vacuum source for a predetermined time, thereby to cause the liquid component of the slurry to pass through the filter element, leaving the solid component deposited on the filter element as a filter cake;
 operating the transport means to displace the sampling device with the filter cake to a measuring station; and
 measuring the physical property of the solid component at the measuring station.

11. A method as claimed in claim 10, in which the filter cake is dried before measuring takes place.

12. A method as claimed in claim 10, in which, after measuring, the filter cake is washed off the filter element.

13. A method as claimed in claim 12, in which the steps of the method are repeated continuously.

14. A method as claimed in claim 10, which is performed automatically.

15. Apparatus for measuring a physical property of the solid component of a slurry, the apparatus comprising:
 a container for the slurry;
 a measuring station provided with a measuring unit;
 a device for use in the preparation of a test sample of the solid component, the device comprising a chamber and a porous wall at least partly bounding the chamber, for supporting a filter element on the face of the element away from the chamber;
 transport means for displacing the device from a sampling position, in which the porous wall is immersed in a slurry in the container, and a measuring position at the measuring station; and
 a vacuum source and means for placing the vacuum source in communication with the chamber of the device to cause, in operation, when the device is in the sampling position, the liquid component of the slurry to pass through a filter element on the porous wall of the device leaving the solid component deposited on the filter element as a filter cake, said apparatus further comprising means for supplying washing liquid to the chamber in the device to provide back washing through the filter element; and
 a flexible pipe connected to the connector means of the device, the flexible pipe being connectable selectively to the vacuum source and to a source of washing liquid.

* * * * *